(12) United States Patent
O'Brien et al.

(10) Patent No.: US 8,297,302 B2
(45) Date of Patent: Oct. 30, 2012

(54) FLOW CELL SPRAY RING

(75) Inventors: Paul J. O'Brien, East Aurora, NY (US); Thomas M. Canty, Williamsville, NY (US)

(73) Assignee: J. M. Canty, Inc., Buffalo, NY (US)

( * ) Notice: Subject to any disclaimer, the term of this patent is extended or adjusted under 35 U.S.C. 154(b) by 324 days.

(21) Appl. No.: 12/749,795

(22) Filed: Mar. 30, 2010

(65) Prior Publication Data

US 2011/0240134 A1 Oct. 6, 2011

(51) Int. Cl.
*F16K 51/00* (2006.01)
*G02B 23/00* (2006.01)
*G02B 23/26* (2006.01)
*G01N 1/10* (2006.01)

(52) U.S. Cl. ......... 137/240; 385/138; 356/246; 362/562
(58) Field of Classification Search .................. 356/246; 385/138; 73/324; 134/6; 222/156–159; 137/240
See application file for complete search history.

(56) References Cited

U.S. PATENT DOCUMENTS

| | | | |
|---|---|---|---|
| 2,744,487 A | 5/1956 | Moore et al. | |
| 3,299,851 A | 1/1967 | Olsen | |
| 3,837,226 A | 9/1974 | Kawawa | |
| 4,245,566 A | 1/1981 | Shimansky et al. | |
| 4,809,862 A | 3/1989 | Canty | |
| 4,977,418 A | 12/1990 | Canty | |
| 6,104,483 A | 8/2000 | Sebok et al. | |
| 6,359,742 B1 | 3/2002 | Canty et al. | |
| 6,771,366 B2 * | 8/2004 | Canty et al. | 356/246 |
| 6,782,184 B2 * | 8/2004 | Canty et al. | 385/138 |
| 2007/0242720 A1 * | 10/2007 | Eckles et al. | 372/107 |

* cited by examiner

*Primary Examiner* — Eric Keasel
*Assistant Examiner* — Daphne M Barry
(74) *Attorney, Agent, or Firm* — Leydig, Voit & Mayer, Ltd.

(57) ABSTRACT

A flow cell device for observing a fluid includes a housing defining an inlet and an outlet, a first viewing member, and a second viewing member. The first viewing member, which is disposed in and coupled to the housing, includes a first window and a spray ring. The spray ring includes cleaning ports in fluid communication with a cleaning fluid inlet port. The second viewing member includes a second window and is disposed in and coupled to the housing opposite the first viewing member such that an aperture that is in fluid communication with the inlet and the outlet is defined between the first window and the second window. The spray ring does not extend past a surface of the first window facing the aperture and each of the cleaning ports is oriented such that a fluid provided under pressure to the cleaning ports is ejected toward the second window.

20 Claims, 5 Drawing Sheets

FLOW CELL SPRAY RING

BACKGROUND OF THE INVENTION

1. Field of the Invention

The present invention relates to devices for observing the interior contents of a vessel or process pipeline, and more particularly to a method and apparatus for cleaning a transparent viewing window provided in a wall of the vessel or pipeline

2. Description of the Related Art

In certain industries, production processes and testing are carried out inside sealed vessels. Various devices are used for direct or remote viewing of the interior of a pressure vessel, reaction vessel, process pipeline, or the like. A simple device for this purpose is a transparent viewing window provided in a wall of the vessel or pipeline. By looking through this window, an operator can observe liquid levels, color changes, and other visually determinable factors taking place within the vessel or pipe. Several of these viewing windows are disclosed, for example, in U.S. Pat. Nos. 2,744,487; 3,299,851; 3,837,226; 4,245,566; 4,809,862; 6,104,483; and 6,359,742. For certain industrial processes, it is desired to use instrumentation, such as imaging and measuring systems in conjunction with a viewing device to provide remote analysis of the process conditions. For example, U.S. Pat. No. 4,977,418 describes a camera viewing device that provides remote viewing of a vessel interior.

U.S. Pat. No. 6,771,366, which is incorporated by reference herein in its entirety, describes a flow cell device system that includes an optical flow cell that enables automatic visual analysis and inspection of fluids for various characteristics including particle size, shape, color, and count, among others. The system includes two viewing ports, each containing a transparent glass window to allow illumination and/or viewing of a fluid in an aperture defined between the two viewing ports.

A problem associated with viewing windows of the prior art is that an internal surface of the viewing window can become coated over or obscured by process constituents coming into contact with the viewing window. This situation can occur when internal fluids are highly viscous or stop flowing for any reason.

U.S. Pat. No. 6,782,184, which is incorporated by reference herein in its entirety, describes a spray ring device that provides for cleaning of an internal process window. The spray ring extends forward of the process surface of the glass in order to allow for cleaning fluid to be sprayed back onto the glass to provide a cleaning function.

The conventional spray ring configuration causes a pocket in the flow of product in front of the viewing window. In many processes, such a pocket will allow material to pool and stick to the window and obstruct the view through the window. The pocket may also prohibit the use of the flow cell in applications where the gap between the viewing window and the illuminating window is required to be quite small. For example, the viewing window and the illuminating window may be required in certain applications to be extremely close to one another to achieve sufficient light penetration for an acceptable image to be captured by a camera through the viewing window. In addition, the pocket in front of the window may cause eddy currents to be created such that the same fluid is trapped in front of the window for an extended period of time, which would cause erroneous analysis results.

Thus, a need exists for a spray ring that can be used to clean the windows in a flow cell having a flow path between two highly polished windows such that no crevices or pockets are created between the windows for particulates to build up in and the gap between the windows can be extremely small.

SUMMARY

The present invention provides a flow cell device for observing a fluid, the flow cell device includes a housing defining an inlet and an outlet, a first viewing member, and a second viewing member. The first viewing member is disposed in and coupled to the housing. The first viewing member includes a first window and a first spray ring disposed around a periphery of the first window. The first spray ring includes a plurality of cleaning ports in fluid communication with a cleaning fluid inlet port disposed in the housing. The second viewing member includes a second window and is disposed in and coupled to the housing opposite the first viewing member such that an aperture is defined between the first window and the second window. The aperture is in fluid communication with the inlet and the outlet. The first spray ring does not extend past a surface of the first window facing the aperture and each of the plurality of cleaning ports is oriented within the first spray ring such that a cleaning fluid provided under pressure to the cleaning fluid inlet port is ejected from the cleaning port toward the second window.

BRIEF DESCRIPTION OF THE DRAWINGS

Exemplary embodiments of the invention are described in the following with respect to the drawings, in which.

DETAILED DESCRIPTION

In accordance with an embodiment of the present invention, a spray ring is incorporated into a flow cell such that no crevices or pockets are created between the windows for particulates to build up in and the gap between the windows can be extremely small.

Figure 1:
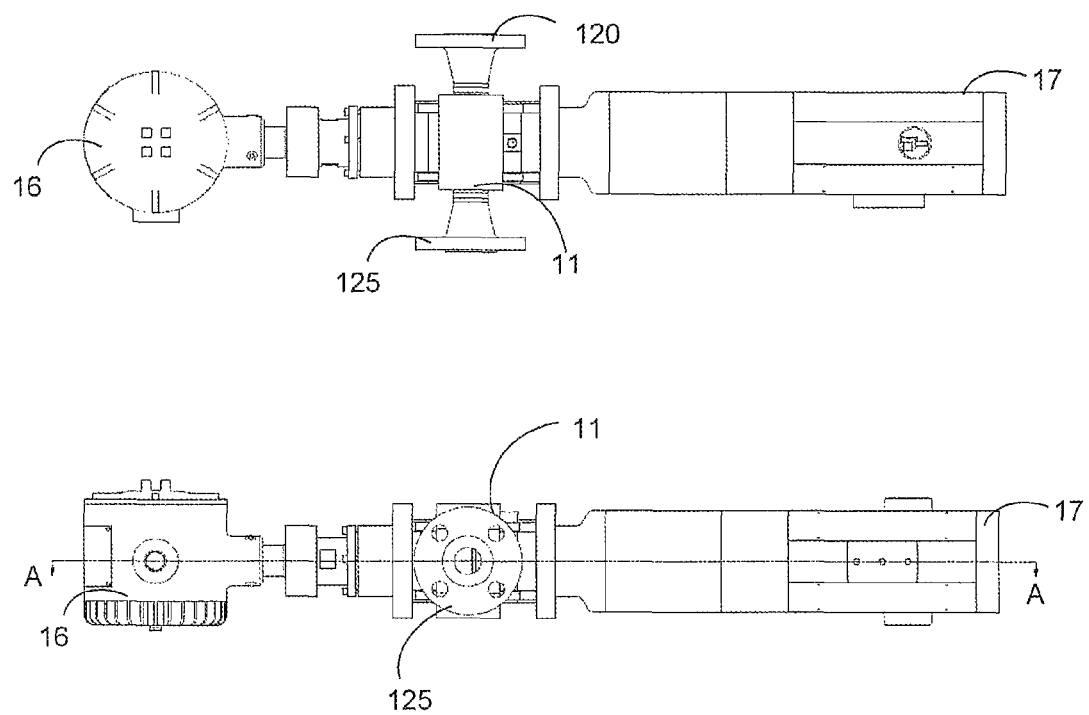
FIG. 1 shows top and side views of one embodiment of flow cell device according to an embodiment of the present invention.
Figure 2:
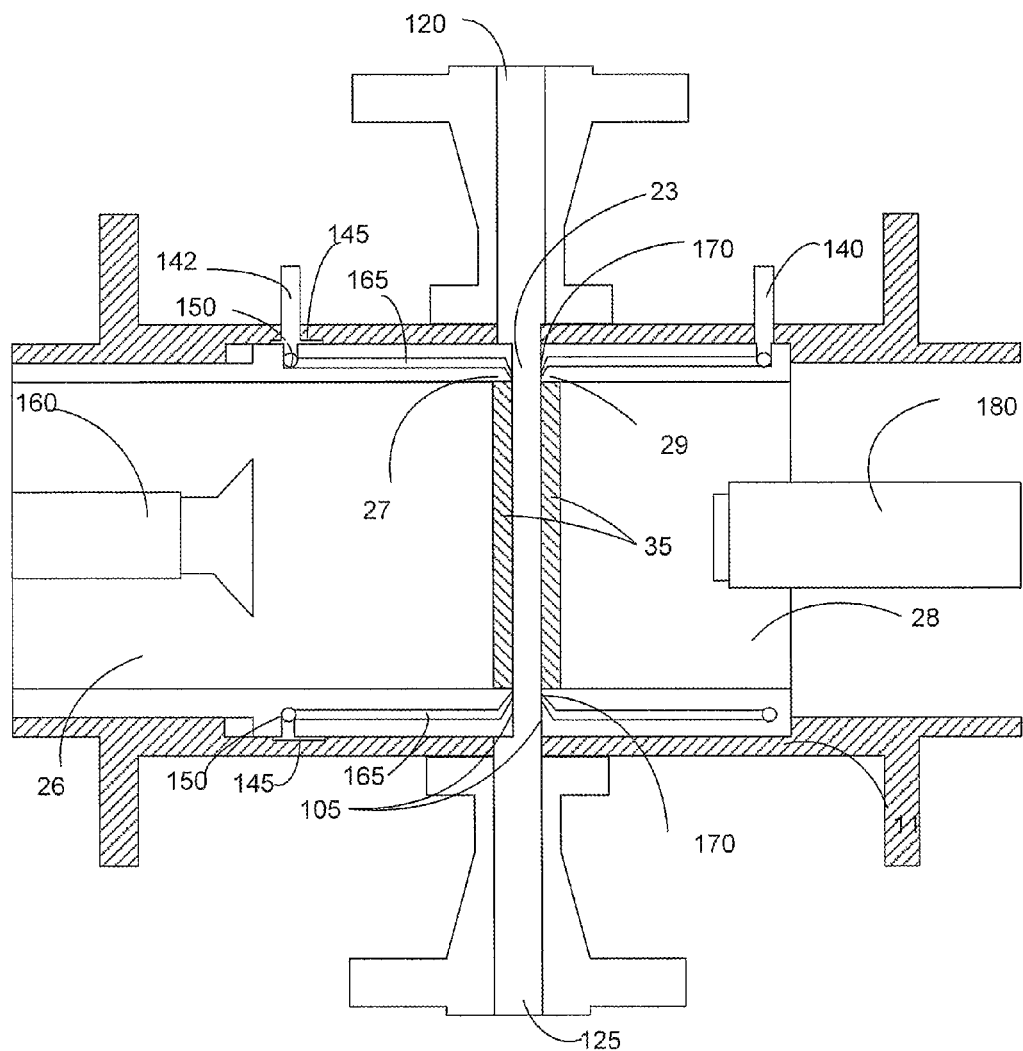
FIG. 2 shows a partial cross sectional view of the flow cell along line A-A of FIG. 1.

Referring now to FIGS. 1 and 2, a flow cell device 10 according to the present invention is described. FIG. 1 shows top and side views of one embodiment of flow cell device 10 according to the present invention. Flow cell device 10 includes housing 11, which includes an inlet conduit 120 that is in fluid communication with the interior of housing 11. Housing 11 also includes outlet conduit 125, which is also in fluid communication with the interior of housing 11. The flow cell device includes a light source section 16 and a camera section that are both coupled to the housing 11.

FIG. 2 shows a partial cross section view of the flow cell 10 along line A-A of FIG. 1. The housing includes a first viewing member 26 and a second viewing member 28, which are disposed opposite one another so as to define an adjustable aperture 23 between the first viewing member 26 and the second viewing member 28. Aperture 23 is defined between viewing members 26 and 28 and is in fluid communication with the inlet conduit 120 and the outlet conduit 125. In a preferred embodiment, aperture 23 is adjustable by moving first viewing member 26 with respect to the housing 11. For example, housing 11 and first viewing member may each include a corresponding threaded area (not shown). Thus, by rotating the first viewing member 26, the position of first viewing member 26 is changed with respect to the housing and second viewing member 28, thus changing thickness of aperture 23.

Inlet conduit 120 can be attached, for example using a hose or high pressure pipeline, to an inlet source (not shown). The inlet source may be a laboratory vessel containing a sample fluid, a pipe, an engine, or some other fluid-containing vessel that is integral with an ongoing industrial process. Likewise, outlet conduit 125 can be attached, for example using a hose or high pressure pipeline to an outlet receptacle (not shown). Again, the outlet receptacle may be a laboratory vessel for holding a sample fluid, a pipe, an engine, or some other fluid-containing vessel that is integral with an ongoing industrial process. Thus, the flow cell device described in the drawings may be used to observe fluid samples in a laboratory setting, or may be installed on-line to observe fluids directly as they occur during an ongoing industrial process. A pump, or other pressure creating device may be used in conjunction with the flow cell device 10, in order to cause the fluid to flow through the device. Alternatively, either gravity or the fluid pressures inherent in the on-line process will cause the desired flow.

Light source 160 may be coupled to first viewing member 26 in order to illuminate the fluid as it flows in the aperture 23. Viewing and illumination can also take place through the same port. Light source 160 may include a light pipe (not shown) that contains fiber optic bundles that carry the light to first viewing member 26. The light source 160 may include an incandescent bulb emitting visible white light. However, a variety of light sources may be used emitting light from across the visible and non-visible spectrum to illuminate the fluid in the aperture. The light source 160 may include any of a number of sources for emitting the light including, for example, various types of light bulbs, lasers, light emitting diodes, reflection of ambient light, and light emitting chemical reactions.

As shown in FIG. 2, after passing through the inlet conduit 120, the fluid enters and passes through the aperture 23. The light source 160 is coupled to first viewing member 26 to illuminate the fluid in aperture 23 and a camera 180 is coupled to second viewing member 28. Thus, in the preferred embodiment, the viewing is performed using the camera 180. Camera 180 may be any kind of camera, such as, for example, a still camera, a video camera, or a CCD camera, and may transmit the image to a remote location, where it can be observed, for example on a video monitor. The image may also be sent as an electronic file to a microprocessor, where various measurements, analysis, and calculations are made to the image information. A person of ordinary skill in the art would recognize that viewing could be performed with or without instrumentation such as a camera from either or both viewing elements. Similarly, illumination of the fluid could be performed, through either or both of the viewing elements, or with no special lighting apparatus, such as allowing ambient light to shine through one or both of the viewing members. Though both members 26 and 28 are referred to as viewing members, it is not necessary that both members enable a viewing of the fluid. In the preferred embodiment, as discussed below, viewing member 28 enables a viewing of the fluid through camera 180, and viewing member 26 enables an illumination of the fluid using light source 160. It is also not necessary that the two viewing members enable either viewing or illumination. For example, one viewing member may be made of solid steel and enable neither, such that viewing and/or viewing and illumination are carried out through the other viewing member.

In a preferred embodiment, first and second viewing members 26, 28 each include a transparent glass window 35 adjacent to aperture 23 to allow illumination and or viewing of the fluid in aperture 23. The glass windows 35 are preferably fused directly to an annular metal frame 27, 29, for example as described in U.S. Pat. No. 6,359,742. Thus, the glass windows 35 can be fused directly to a metal end portion of the respective viewing member 26, 28, shaped to form an annular frame 27 29. Preferably, the construction is sturdy enough to handle fluids having high pressures, such as pressures of up to and exceeding 6000 pounds per square inch (p.s.i.). The sturdy fused glass to metal construction enables a wide field of view for a broader view of the flow stream and thus better analytical accuracy, and a larger flow cell to process more fluid in less time. The sturdy construction also enables the device to be employed in rugged field environments, such as when vibration and other ambient effects are present that might cause a thin glass window flow cell to leak or break.

Each viewing member includes a spray ring 105 surrounding the perimeter of the respective glass windows 35. As shown in FIGS. 2-5, the spray ring 105 may be integral to the annular frame 27, 29. Alternatively, the spray ring 105 may be a separate component. Although described as a ring, the spray ring 105 need not be annular. For example, the spray ring 105 and transparent glass window 35 may be rectangular.

The surface of each window 35 facing the aperture is preferably flush with the surface of the respective spray ring 105. However, the spray ring 35 may alternatively be set back from the surface of the window 35. Because the spray ring is either flush or set back from the window surface with respect to the aperture 23, the flow of fluid in front of the window 35 is unperturbed. Additionally, because the spray ring 35 does not protrude into the aperture 23, the width of the aperture 23 can be adjusted such that a very small space exists between the respective windows of viewing members 26, 28.

When fluid passes through aperture 23, the surface of each of the glass windows 35 facing the aperture 23 can become clouded or blocked by process constituents coming into contact with the window 35. The spray ring is provided as part of the first and second viewing members 26, 28 to clean the windows 35.

Figure 3:
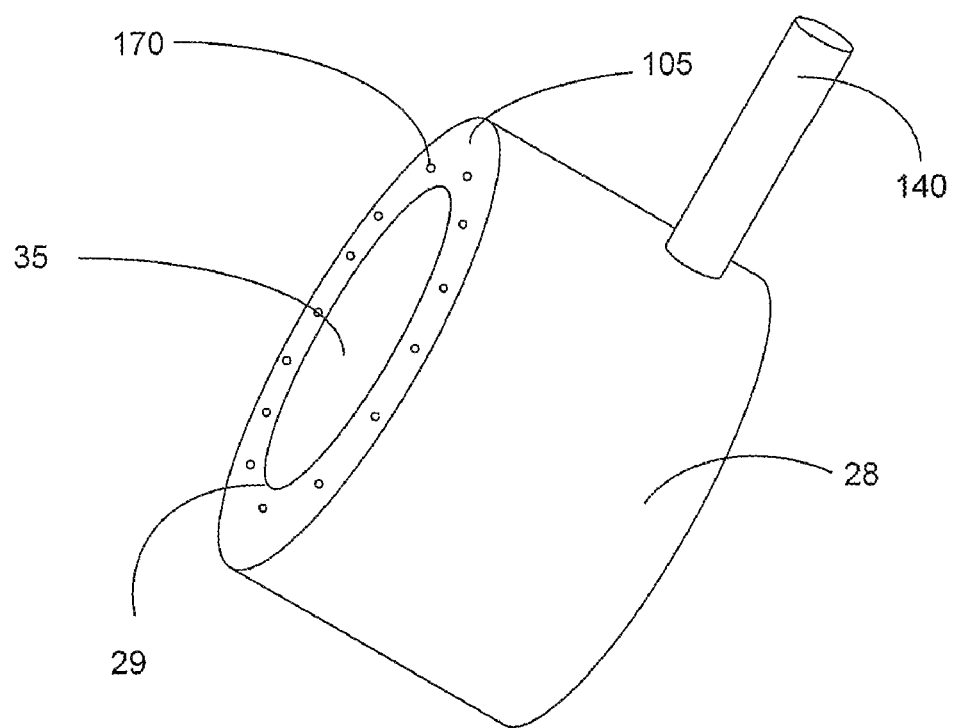
FIG. 3 shows a perspective view of an embodiment of a viewing member incorporating a spray ring in accordance with an embodiment of the invention.
Figure 4:
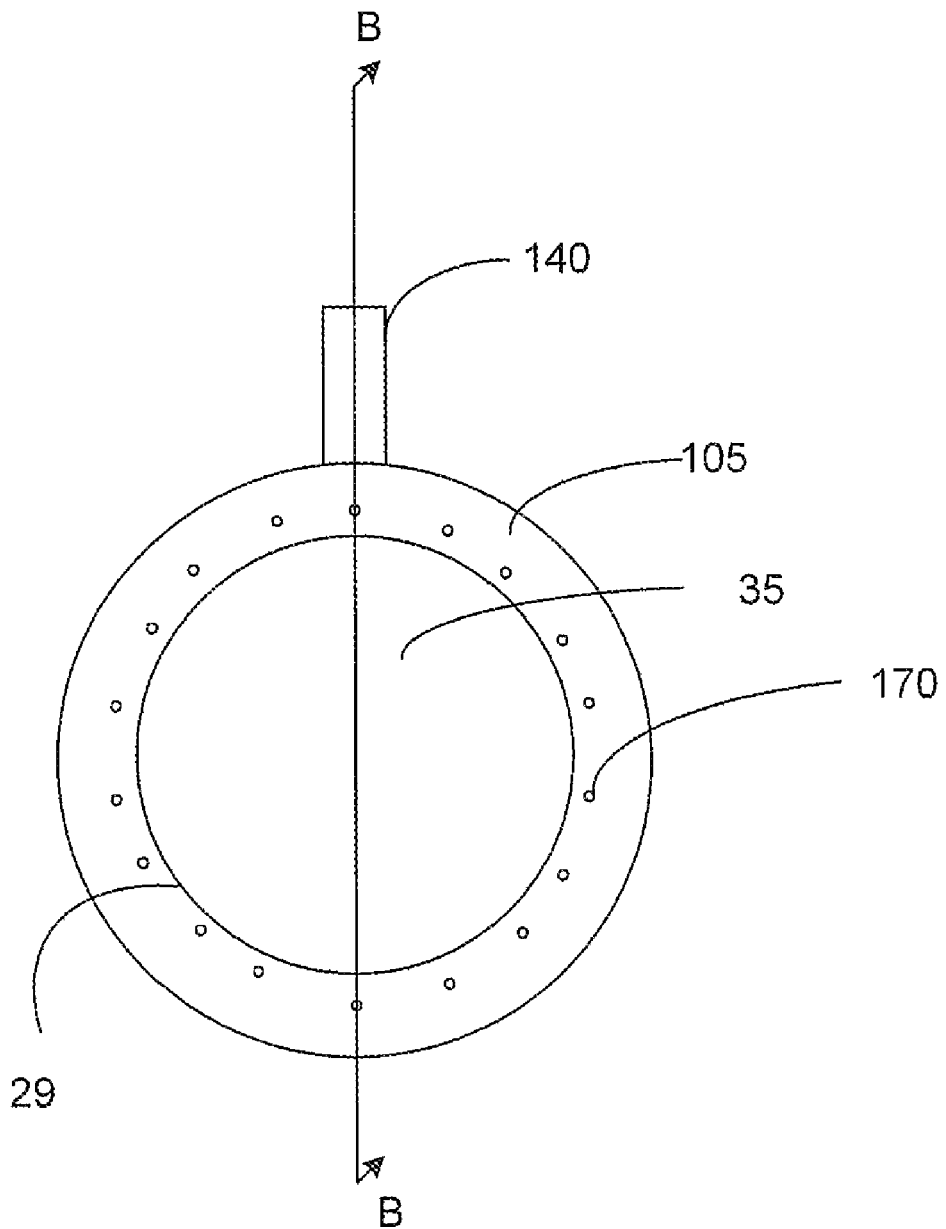
FIG. 4 shows a front view of the viewing member incorporating the spray ring of FIG. 3.

FIGS. 3-4 show a viewing member 28 incorporating a spray ring 105 in accordance with an embodiment of the present invention. As shown in FIG. 3, the viewing member 28 includes a cleaning fluid inlet port 140, a transparent glass window 35, and a spray ring 105. The spray ring 105 includes a plurality of cleaning ports 170 surrounding the transparent glass window 35. Each of the cleaning ports 170 is fluidly connected to the cleaning fluid inlet port 140. Although only a single cleaning fluid inlet port 140 is illustrated, multiple cleaning fluid inlet ports may instead be used to distribute the cleaning fluid to the cleaning ports 170.

Figure 5:
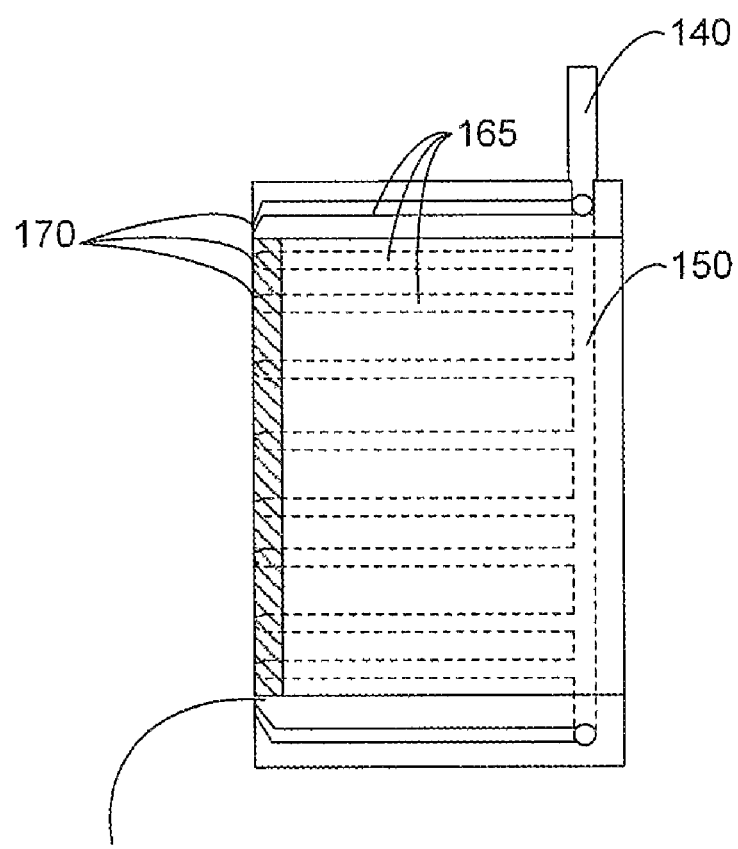
FIG. 5 shows a cross sectional view of the viewing member incorporating a spray ring along line B-B of FIG. 4.

Referring now to FIG. 5, the flow of cleaning fluid from the cleaning fluid inlet port 140 to the cleaning ports 170 is described. FIG. 5 shows a cross sectional view of the viewing member incorporating the spray ring 105 along line B-B of FIG. 4. As illustrated in FIG. 5, the cleaning fluid inlet port 140 is fluidly connected to a fluid distribution channel 150 that distributes the cleaning fluid around the circumference of the viewing member 28. Fluid distribution channel 150 is connected to a plurality of cleaning port feed channels 165, which each are fluidly connected to one or more of the cleaning ports 170.

The cleaning fluid inlet port 140 may be fixed to the viewing member 28 as shown in FIGS. 3-5. Alternatively, as shown in FIG. 2, cleaning fluid inlet port 142 may be fixed to the housing 11. The housing may include a circumferential distribution channel 145 that is located in an interior circumference of the housing, such that fluid can be distributed to the fluid distribution channels 150 when the first viewing member 26 is rotated to thereby adjust the thickness of aperture 23. A person of ordinary skill in the art would recognize that other methods of fluidly connecting the fluid inlet ports 140, 142 to the cleaning ports 170 are possible.

Referring now to FIG. 2, the cleaning of the transparent glass windows 35 is described. Each of the cleaning fluid inlet ports 140, 142 can be attached, for example using a hose or high pressure pipeline, to a source of cleaning fluid. Although shown as having separate cleaning fluid input ports 140, 142, the housing 11 may include only a single cleaning fluid input port that is fluidly connected to the spray rings 105 of both the first and second viewing members 26, 28. A pump or other pressure creating device may be used in conjunction with the cleaning fluid inlet ports 140, 142 in order to cause cleaning fluid to flow at high pressure out of the cleaning ports 170.

As shown in FIG. 2, the cleaning ports 170 are angled within the spray ring 105 such that cleaning fluid ejected from the cleaning ports is directed toward the opposite transparent glass window 35. Each of the cleaning ports 170 may have a different orientation associated with it in order to create a desired spray pattern of cleaning fluid. Additionally, each of the cleaning ports 170 may have a variable diameter, such that the amount of cleaning fluid that is ejected from each cleaning port 170 may vary.

In a preferred embodiment, two spray rings are employed, one for each of the first and second viewing members 26, 28. However, a flow cell employing only a single spray ring 105 is also contemplated. If the aperture 23 is set to be small enough, the spray produced by a single spray ring 105 is violent enough to clean both windows 35.

Further, in the embodiment shown, each of the spray rings 105 is integral with the first and second viewing members 26, 28 respectively. However, this is not a necessary requirement of the invention. As long as the spray ring 105 does not create a physical obstruction of the fluid flow path in the aperture 23 between the transparent windows 35, the fluid will flow properly through the gap between the two windows 35. Thus, the spray ring 105 need not be integral with the viewing member but may instead be, for example, a separate component surrounding the viewing member.

While the invention has been particularly shown and described with reference to preferred embodiments thereof, it will be understood by those skilled in the art that various changes in form and details may be made therein without departing from the spirit and scope of the invention.

We claim:

1. A flow cell device for observing a fluid comprising:
a housing defining an inlet and an outlet;
first and second viewing members disposed opposite one another in the housing so as to form an aperture between the first and second viewing members that is in fluid communication with the inlet and the outlet,
the first viewing member comprising a first window having a first surface facing the aperture and a first spray ring disposed around a periphery of the first window, the first spray ring including a first plurality of cleaning ports in fluid communication with a cleaning fluid inlet port disposed in the housing; and
the second viewing member comprising a second window opposite the first window,
wherein the first spray ring does not extend toward the second viewing member past the first surface of the first window and each of the first plurality of cleaning ports is oriented within the first spray ring such that when a cleaning fluid is provided under pressure to the cleaning fluid inlet port, the cleaning fluid is ejected from each of the first plurality of cleaning ports across an entire width of the aperture to the second window.

2. The flow cell device of claim 1, wherein the first spray ring is flush with the first surface of the first window facing the apetture.

3. The flow cell device of claim 1, wherein the second viewing member is movably coupled to the housing such that a width of the aperture is variable.

4. The flow cell device of claim 1, wherein the first window is fused to a metal portion of the first viewing member and the first spray ring is integral to the metal portion of the first viewing member.

5. The flow cell device of claim 1, wherein a spray pattern for the first spray ring is determined by a number of the first plurality of cleaning ports, and a size and the orientation of each of the first plurality of cleaning ports.

6. The flow cell device as recited in claim 1 further comprising a camera coupled to the first viewing member configured to record an image of a fluid in the aperture through the first window.

7. The flow cell device as recited in claim 1 further comprising a light source coupled to the second viewing member configured to provide an illumination of a fluid in the aperture through the second window.

8. The flow cell device of claim 1, wherein the second viewing member comprises a second spray ring disposed around a periphery of the second window, the second spray ring not extending past a surface of the second window facing the aperture, the second spray ring including a second plurality of cleaning ports in fluid communication with the cleaning fluid inlet port,
wherein each of the second plurality of cleaning ports is oriented within the second spray ring such that when the cleaning fluid is provided under pressure to the cleaning fluid inlet port, the cleaning fluid is ejected from each of the second plurality of cleaning ports toward the first window.

9. The flow cell device of claim 8, wherein the first spray ring is flush with the surface of the first window facing the aperture and the second spray ring is flush with the surface of the second window facing the aperture.

10. The flow cell device of claim 8, wherein the second viewing member is movably coupled to the housing such that a width of the aperture is variable.

11. The flow cell device of claim 8, wherein the first window is fused to a metal portion of the first viewing member and the first spray ring is integral to the metal portion of the first viewing member, and
wherein the second window is fused to a metal portion of the second viewing member and the second spray ring is integral to the metal portion of the second viewing member.

12. The flow cell device of claim 8, wherein a spray pattern for the first spray ring is determined by a number of the first plurality of cleaning ports, and a size and the orientation of each of the first plurality of cleaning ports, and
wherein a spray pattern for the second spray ring is, determined by a number of the second plurality of cleaning ports, and a size and the orientation of each of the second plurality of cleaning ports.

13. The flow cell device as recited in claim 8 further comprising a camera coupled to the first viewing member configured to record an image of a fluid in the aperture through the first window.

14. The flow cell device as recited in claim 8 further comprising a light source coupled to the second viewing member configured to provide an illumination of a fluid in the aperture through the second window.

15. A method for cleaning a fluid flow cell, the method comprising:

provoding a fluid flow cell including a housing having an inlet and an outlet and first and second viewing members disposed opposite one another in the housing so as to form an aperture between the first and second viewing members that is in fluid communication with the inlet and the outlet, the first viewing member including a first window having a first surface facing the aperture and a first spray ring disposed around a periphery of the first window, the second viewing member including a second window opposite the first window, wherein the first spray ring does not extend toward the second viewing member past the first surface; and passing a cleaning fluid under pressure through a first plurality of cleaning ports in the first spray ring such that the cleaning fluid is ejected from each of the first plurality of cleaning ports across an entire width of the aperture onto the second, window of the second viewing member.

16. The method of claim 15, wherein the first spray ring is flush with the surface of the first window facing the aperture.

17. The method of claim 15, further comprising, passing a second fluid into the inlet, through the aperture and out of the outlet.

18. The method of claim 15, further comprising, passing the cleaning fluid under pressure through a second plurality of cleaning ports in a second spray ring disposed around a periphery of the second window of the second viewing member such that the cleaning fluid is ejected from the second plurality of cleaning ports toward the first window, wherein the second spray ring does not extend pasta surface of the second window facing the aperture.

19. The method of claim 18, wherein the first spray ring is flush with a surface of the first window facing the aperture and the second spray ring is flush with a surface of the second window facing the aperture.

20. The method of claim 18, further comprising, passing a second fluid into the inlet, through the aperture and out of the outlet.

* * * * *